United States Patent [19]

Lavault et al.

[11] Patent Number: 5,352,757
[45] Date of Patent: Oct. 4, 1994

[54] SULFUR COMPOUNDS AND NEW POLYMERS OBTAINED FROM THESE SULFUR COMPOUNDS

[75] Inventors: Sylvie Lavault, Lyons; Gérard Velleret, Paris, both of France

[73] Assignee: Rhone-Poulenc Chimie, Courbevoie, France

[21] Appl. No.: 920,363

[22] Filed: Sep. 16, 1992

[30] Foreign Application Priority Data

Dec. 14, 1990 [FR] France ............................... 90 15977

[51] Int. Cl.[5] ............................................. C08G 18/77
[52] U.S. Cl. ...................................... 528/80; 528/376; 560/147
[58] Field of Search .................. 528/80, 376; 560/147

[56] References Cited

U.S. PATENT DOCUMENTS

| 3,397,189 | 8/1968 | Erickson et al. | 528/376 |
| 3,661,744 | 5/1972 | Kehr et al. | 528/376 |

FOREIGN PATENT DOCUMENTS

| 490777 | 6/1992 | European Pat. Off. | 560/147 |
| 4300864 | 10/1992 | Japan | 560/147 |

*Primary Examiner*—John Kight, III
*Assistant Examiner*—Rachel Johnson
*Attorney, Agent, or Firm*—Finnegan, Henderson, Farabow & Dunner

[57] ABSTRACT

The present invention relates to new sulfur compounds which are polyol esters of mercaptocarboxylic acids. It also relates to the use of these sulfur esters for preparing polymers exhibiting a refractive index higher than 1.50. The manufacture of optical discs and of waveguides may be mentioned among the optical applications of these polymers.

33 Claims, No Drawings

SULFUR COMPOUNDS AND NEW POLYMERS OBTAINED FROM THESE SULFUR COMPOUNDS

The present invention relates to new sulfur compounds which are polyol esters of mercaptocarboxylic acids.

It also relates to the use of these sulfur esters for preparing polymers exhibiting a refractive index higher than 1.50.

Many routes have been proposed for obtaining this result.

One of the most promising ones is the use of monomer comprising one or more sulfur atoms.

The present invention consists firstly of the sulfur compounds of general formula (I):

  (I)

in which:

$R_1$ denotes a linear or branched alkylene radical containing 1 to 3 carbon atoms;

A denotes a hydrocarbon residue of valency n, chosen from the radicals of formulae:

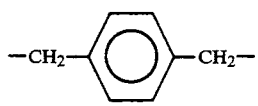  (II)

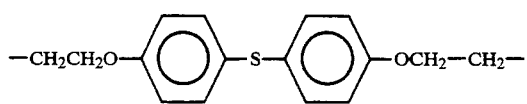  (III)

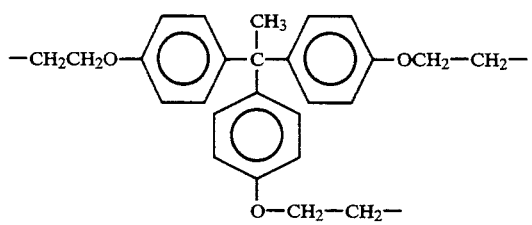  (IV)

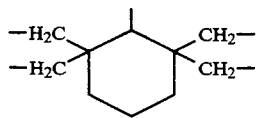  (V)

n denotes 2, 3 or 5.

Among the sulfur compounds of formula (I), those most frequently preferred are the ones in which $R_1$ denotes a methylene radical, an ethylene radical or an ethylidene radical.

There may thus be mentioned: 1,4-benzenedimethylene di(thioglycolate), 4,4'-thiodiphenylene, 1,1'-oxyethyl di(thioglycolate), 1,1,1-tris(4-phenylene-1-oxyethyl)ethane tri(thioglycolate), 2,2,6,6-tetramethylenecyclohexyl penta(thioglycolate), 1,4-benzenedimethylene di(2-mercaptopropionate), 4,4'-thiodiphenylene-1,1'-oxyethyl di(2-mercaptopropionate), 1,1,1-tris(4-phenylene-1-oxyethyl)ethane tri(2-mercaptopropionate) and 2,2,6,6-tetramethylenecyclohexyl penta(2mercaptopropionate).

The compounds of formula (I) are prepared in a known manner by esterifying a polyol of formula (VI) A-(OH)$_n$ with the mercaptocarboxylic acid of formula (VII) HS-$R_1$COOH, in which the symbols A, n and $R_1$ have the meanings given for formula (I), in the presence of the usual catalysts for this type of reaction.

They can also be prepared by transesterification between a polyol A—(OH)$_n$ and an ester of an alcohol of low boiling point (in most cases a methanol ester) of the mercaptocarboxylic acid HS—$R_1$—COOH, in the presence of the usual transesterification catalysts.

The sulfur compounds of formula (I) are especially suitable for the preparation of polythiourethanes by reaction between at least one of the said compounds (I) and at least one polyisocyanate.

The sulfur compounds of formula (I) may be employed mixed with known polythiols.

Examples of such polythiols which may be mentioned are pentaerythrityl tetra(thioglycolate), pentaerythrityl tetra(2-mercaptopropionate), trimethylolpropane tri(thioglycolate), trimethylolpropane tri(2-mercaptopropionate), 1,2-benzenedithiol, 1,4-benzenedithiol, dipentaerythritol hexa(thioglycolate) and 1,3,5-tri( 3-mercaptopropyl) isocyanurate.

Reference may also be made to other polythiols such as light compounds e.g. dimercaptopropanol, dithioerythritol, trithioglycerine, tetramercaptobutane, pentaerythrithiol and to those mentioned in the patent EP-A-0,351,073.

The preferred thiol constituents - other than those according to the invention - are nonester acyclic saturated monomers bearing at least three functional groups which react with isocyanates to form carbamate bonds, among which reactive functional groups at least 40% of their number are mercaptan SH groups, the proportion of the said functional groups being at least 45% on a mass basis relative to the molecular mass of the said monomer.

There is no particular limitation in the case of the polyisocyanates used to prepare the said polythiourethanes.

These are polyisocyanates properly so called, such as, for example, toluene diisocyanate, 4,4'-diisocyanatodiphenylmethane, polymeric 4,4'-diisocyanatodiphenylmethane, hexamethylene diisocyanate, 2-methyl-1,5-diisocyanatopentane, 2-ethyl-1,4-diisocyanatobutane, isophorone diisocyanate, xylylene diisocyanate, 4,4'-diisocyanatodicyclohexylmethane and hydrogenated xylylene diisocyanate.

They are also trimers containing an isocyanurate ring or biurets of such polyisocyanates.

Among the polyisocyanates preference will be given to those in whose formula the —NCO functional groups are not bonded directly to an aromatic ring, because polythiourethanes prepared from aromatic polyisocyanates tend to be colored.

Furthermore, it is quite obvious that among the polyisocyanates those chosen will themselves already have a sufficiently high refractive index, like, for example, xylylene diisocyanate.

It is thus preferred to employ a polyisocyanate which has a refractive index equal to or higher than 1.53.

The reaction between the sulfur compounds of formula (I) and the polyisocyanates takes place under the usual conditions for this type of reaction.

An organic tin compound is generally employed as catalyst, in most cases dibutyltin dilaurate.

The sulfur compounds of formula (I) are also employed for preparing polythioethers by reaction with at least one compound containing at least two ethylenic unsaturations.

For example, unsaturated compounds which may be mentioned are triallyl isocyanurate, triallyl cyanurate, diallyl phthalate, divinylbenzene, trimethallyl thiocyanurate, 2-hydroxyethyl cyanurate triacrylate, 2-hydroxyethyl cyanurate trimethacrylate, 2-hydroxyethyl cyanurate tri(allylcarbonate), 2-hydroxyethyl cyanurate tri(methallylcarbonate) and 2,2-bis(4-hydroxyphenyl)-propane diacrylate.

Among these unsaturated compounds preference will be given to those which have the greatest number of ethylenic unsaturations and those which themselves have a sufficiently high refractive index.

If the number of ethylenic unsaturations is not greater than 2, it will be preferable to use a ternary mixture of polythiol/diunsaturated/triacrylate or trimethacrylate in order to have a hard glass. The triacrylates or trimethacrylates are, for example, trimethylolpropane triacrylate, pentaerythritol triacrylate, pentaerythritol trimethacrylate, dipentaerythritol hexacrylate or dipentaerythritol hexamethacrylate.

The reaction between the sulfur compounds of formula (I) and the compounds containing ethylenic unsaturations takes place with an excess of ethylenic unsaturations relative to the thiol functional groups.

A certain slowness of the polymerisation has, in fact, been revealed when the quantity of thiol functional groups is increased.

This preparation generally takes place in the presence of catalysts such as peroxides and, more generally, radical-generators.

From 0.1% to 10% by weight of catalyst is generally employed relative to the weight of the reaction mixture.

The polythiourethanes and the polythioethers obtained from the sulfur compounds of formula (I) have properties which enable them to be employed in optics.

In fact, these polymers have a refractive index which is higher than 1.50 and an Abbe number higher than or equal to 30, and this indicates a low dispersion.

Alone or mixed, these polymers form materials which is [sic] very useful for many optical utilizations including the manufacture of opthalmic lens [sic].

These materials do not deteriorate with time, either due to light or due to inclement weather (yellowing or losses of mechanical property [sic]) and they exhibit a good impact strength to abrasion [sic] they can be colored and is [sic] easy to demold.

The manufacture of optical discs and of waveguides may be mentioned among the optical applications.

EXAMPLES

Example 1: Preparation of 1,4-benzenedimethylene di(thioglycolate)

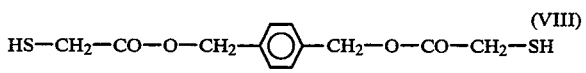

Into a 2-liter three-necked round bottom flask fitted with a central stirrer, a thermometer pocket and a "Dean Stark" [sic] supporting a condenser under nitrogen blanketing are charged:
- 138.2 g (1.0 mol) of 1,4-benzenedimethanol
- 239.5 g (2.6 mol) of distilled thioglycolic acid
- 3.5 g of para-toluenesulfonic acid
- 1,000 cm³ of toluene.

The mixture is heated to reflux (110°–112° C.) with stirring for 1 h 45 min; 37 cm³ of water are collected in the bottom part of the "Dean Stark" [sic].

The reaction mixture is allowed to cool to room temperature and is then washed with 5×500 cm³, and then with 2×1,000 cm³, of water.

The organic phase is dried over $Na_2SO_4$, is filtered, and is then concentrated under reduced pressure.

274 g (approximately 96% yield relative to the starting diol) of a viscous, colorless liquid which has a refractive index $n_D = 1.5665$, are thus obtained.

The spectrum obtained by proton NMR corresponds to the expected structure.

Determination of the —SH functional groups using 0.1 N sodium hydroxide gives 692 milliequivalents (meq) per 100 g.

MANUFACTURE OF OPTHALMIC LENSES

The composition employed comprises:
Xylylene diisocyanate (XDI) : 9.4 g (0.05 mol)
Trithioglycerine : 2.38 g (0.0172 mol)
1,4-Benzenedimethylene dithioglycolate : 6.86 g (0.024 mol) $(HS-(CH_2)_2-CO-O-CH_2-pC_6H_4-CH_2-OCO-CH_2-SH)$ The molar proportion of trithioglycerine in the molar total of monomers is 42%.

The product obtained has the following properties:
refractive index : 1.65
constringence ( Abbe number ) : 30
glass transition temperature : 95° C.

Other Manufactures of lenses

The composition employed comprises:
Xylylene diisocyanate (XDI) : 9,4 g (0,05 mol)
Dimercaptopropanol (DMP) : 2.23 g (0,018 tool)
Benzenedimethylene para-thioglycolate : 10,03 g (0,024 mol) ( ( $HS-CH_2-COO-CH_2-S-pC_6H_4-CH_2-OCO-CH_2-SH$)

The molar proportion of DMP in the molar total of the monomers is 41%.

The product obtained has the following properties:
refractive index : 1.63
constringence (Abbe number) : 33
glass transition temperature : 100° C.

Example 2: Preparation of 4,4'-thiodipenylene-1,1'-oxyethyl di(thioglycolate)

A) Ethoxylation of 4,4'-thiodiphenol to 1,1'-di(2-hydroxyethoxy)-4,4'-thiodiphenylene(IX)

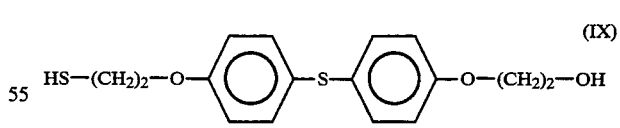

Into a 2-liter three-necked round bottom flask fitted with a central stirrer, a thermometer pocket and a condenser under nitrogen blanketing are charged:
- 196.4 g (0.90 mol) of 4,4'-thiodiphenol
- 194.3 g (2.21 mol) of ethylene carbonate
- 3.9 g of potassium carbonate
- 900 cm³ of toluene.

The mixture is heated with stirring to reflux (approximately 112° C.) for 24 hours.

The reaction mixture is then filtered when hot; the filtrate crystallizes on cooling.

The solid which has precipitated out is filtered off on a sintered glass filter and is washed with petroleum ether (2×1,000 cm$^3$) and then with water (2×1,000 cm$^3$).

It is then dried under reduced pressure at 60°–80° C.

257.2 g (93% yield relative to the thiodiphenol introduced) of a white powder are obtained, whose melting point is 95°–97° C.

The expected structure is confirmed by proton NMR.

B) Preparation of 4,4'-thiodiphenylene-1,1'-oxyethyl di(thioglycolate)

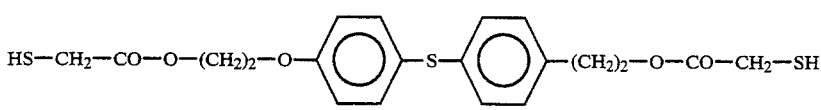

Into a 2-liter three-necked round bottom flask fitted with a central stirrer, a thermometer pocket, a "Dean Stark" [sic] supporting a condenser under nitrogen blanketing are charged:
  245.1 g (0.8 mol) of 1,1'-di(2-hydroxyethoxy)-4,4'-thiodiphenylene prepared in A
  191.6 g (2.08 mol) of distilled thioglycolic acid
  2.0 g of para-toluenesulfonic acid
  1,000 cm$^3$ of toluene.

The mixture is heated to reflux (110°–112° C.) with stirring for 1 h 30 min; 29 cm$^3$ of water are collected in the lower part of the "Dean Stark" [sic].

The reaction mixture is allowed to cool to room temperature and is then washed with 7×1,000 cm$^3$ of water.

80 g of Na$_2$SO$_4$ and 70 g of activated alumina are added to the organic phase. After stirring for 45 min, 7 g of Clarcel are added. Stirring is then continued for 5 min at 8,000 rev/min.

The material is filtered and concentrated under reduced pressure.

334 g (approximately 92% yield relative to the starting diol) of a viscous, colorless liquid which has a refractive index $n_D$=1.608 are thus obtained; this crystallizes little by little to a solid white product.

The spectrum obtained by proton NMR corresponds to the expected structure.

Determination of the —SH functional groups using 0.1N sodium hydroxide gives 423 meq SH/100 g.

MANUFACTURE OF OPTHALMIC LENSES

The composition employed comprises:
Xylylene diisocyanate (XDI) : 9.4 g (0.05 mol)
Trithioglycerine : 2.38 g (0.0266 mol)
4,4'-Thiodiphenylene-1,1'-oxyethyl para-dithioglycolate : 10.03 g (0.024 mol)

The molar proportion of trithioglycerine in the molar total of the monomers is 42%.

The product obtained has the following properties:
refractive index : 1.66
constringence (Abbe number) : 29
glass transition temperature : 100° C.

Other Manufactures of lenses

The composition employed comprises:
Xylylene diisocyanate (XDI) : 9.4 g (0.05 mol)
Dimercaptopropanol (DMP) : 2.23 g (0.018 mol)
4,4'-Thiodiphenylene-1,1'-oxyethyl para-dithioglycolate : 10.03 g (0,024 mol)

The molar proportion of DMP in the molar total of the monomers is 43%.

The product obtained has the following properties:
refractive index : 1.63
constringence (Abbe number) : 32
glass transition temperature : 100° C.

Example 3: Preparation of Al Ethoxylation of 1,1,1-tris(4-hydroxyphenyl)ethane to 1,1,1-tris [-I-2-hydroxyethoxy)phenyl]ethane (XI) [sic]

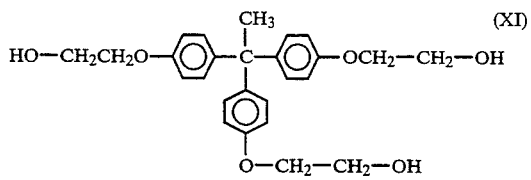

Into a 0.5-liter three-necked round bottom flask fitted with a central stirrer, a thermometer pocket and a condenser under nitrogen blanketing are charged:
  49.2 g (0.16 mol) of 1,1,1-tris(4-hydroxyphenyl)ethane
  50.8 g (0.576 mol) of ethylene carbonate
  1 g of potassium carbonate
  250 cm$^3$ of toluene
  300 cm$^3$ of dioxane.

The mixture is heated to reflux with stirring for 36 hours.

The reaction mixture is then filtered when hot; the filtrate (violet-pink) is concentrated under reduced pressure. The colored residue begins to crystallize.

It is taken up with 250 cm$^3$ of dichloromethane.

It is filtered on a sintered glass filter, and is washed with dichloromethane (400 cm$^3$).

It is then dried under reduced pressure.

63.4 g (90% yield relative to the triphenol introduced) of a light-ochre powder whose melting point is 50° C. are obtained.

The expected structure is confirmed by proton NMR.

B) Preparation of 1,1,1-tris(4-phenylene-1-oxyethyl) tri(thipglycolate)

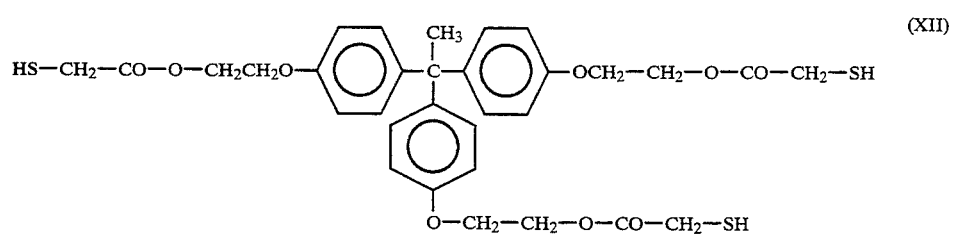

Into a 250-cm³ three-necked round bottom flask fitted with a central stirrer, a thermometer pocket and a "Dean Stark" [sic] supporting a condenser under nitrogen blanketing are charged:

43.9 g (0.1 mol) of 1,1,1-tris[1-(2-hydroxyethoxy)-phenyl]ethane prepared in 3 A 48 g (0.52 mol) of distilled thioglycolic acid 0.2 g of para-toluenesulfonic acid 100 cm³ of toluene.

The mixture is heated to reflux with stirring for 1 h 30 min.

The reaction mixture is allowed to cool to room temperature and is then washed with 5×100 cm³ of water.

The organic phase is dried over Na₂SO₄ and is treated with active carbon (5 g) when hot and is then concentrated under reduced pressure.

59.7 g (approximately 87% yield relative to the starting triol) of a slightly cloudy, very slightly yellow and highly viscous liquid which has a refractive index $n_D = 1.5985$ are thus obtained.

The spectrum obtained by proton NMR corresponds to the expected structure.

Determination of the —SH functional groups using 0.1N sodium hydroxide gives 432 meq SH/100 g.

MANUFACTURE OF OPTHALMIC LENSES

The composition employed comprises:
Xylylene diisocyanate (XDI) : 9.4 g (0.05 mol)
Trithioglycerine : 0.84 g (0.0266 mol)
1,1,1-Tris(4-phenylene-1-oxyethyl)ethane trithioglycolate : 14.5 g (0.022 mol) ((HS—(CH₂)₂—O—CO—CH₂—S)₂HC—pC₆H₄—CH(—S—CH₂—COO—(CH₂)₂—SH)₂)

The molar proportion of trithioglycerine in the molar total of the monomers is 21%.

The product obtained has the following properties:
refraction index : 1.66
constringence (Abbe number) : 30
glass transition temperature : 100° C.

Other Manufactures of lenses

The composition employed comprises:
Xylylene diisocyanate (XDI) : 9.4 g (0.05 mol)
Dimercaptopropanol (DMP) : 0.98 g (0.007 mol)
b  1,1,1-Tris(4-phenylene-1-oxyethyl)ethane trithioglycolate : 15.84 g (0.024 mol)

The molar proportion of DMP in the molar total of the monomers is 27%.

The product obtained has the following properties:
refractive index : 1.64
constringence (Abbe number) : 30
glass transition temperature : 115° C.

Example 4: Preparation of 2,2,6,6-tetramethylene-cyclohexyl pentapolyglycolate

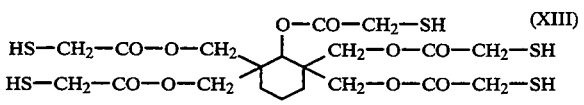

Into a 100 cm³ three-necked round bottom flask fitted with a central stirrer, a thermometer pocket and a "Dean Stark" [sic] supporting a condenser under nitrogen blanketing are charged:

11 g (0.05 mol) of 2,2,6,6-tetra(hydroxymethyl)cyclohexanol 34.5 g (0.375 mol) of distilled thioglycolic acid 0.15 g of para-toluenesulfonic acid 50 cm³ of toluene.

The mixture is heated to reflux (110°–115° C.) with stirring for 6 h; 4.6 cm³ of water are collected in the lower part of the "Dean Stark" [sic].

The reaction mixture is allowed to cool to room temperature and is then washed with 7×30 cm³ of water.

The organic phase is dried over Na₂SO₄, is filtered and is concentrated under reduced pressure.

24.4 g (approximately 81% yield relative to the starting polyol) of a viscous, colorless liquid which has a refractive index $n_D = 1.558$ are thus obtained.

Determination of the —SH functional groups using 0.1N sodium hydroxide gives 767 meq SH/100 g (theory: 968 meq SH/100 g).

The presence of two products is determined by mass spectrometry:
the expected product of formula (XIII) (predominant)
the product of following formula (XIV):

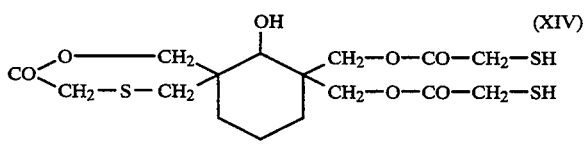

10 g of this mixture of products are purified by preparative high performance liquid chromatography.

The 2 pure products (XIII) and (XIV) are recovered:
5.6 g of product (XIII) : $n_D = 1.545$
3.5 g of product (XIV) : $n_D = 1.5455$ These products are characterized by mass spectrometry.

MANUFACTURE OF OPTHALMIC LENSES

The composition employed comprises:
Xylylene diisocyanate (XDI) : 9.4 g (0.05 mol)
Trithioglycerine : 0.84 g (0.0266 mol)
2,2,6,6-Tetramethylenecyclohexyl pentapolyglycolate : 5.9 g (0.01 mol)

The molar proportion of trithioglycerine in the molar total of the monomers is 63%.

The product obtained has the following properties:
refractive index : 1.65
constringence (Abbe number) : 32
glass transition temperature : 120° C.

Other Manufactures of lenses

The composition employed comprises:
Xylylene diisocyanate (XDI) : 9.4 g (0.05 mol)
Dimercaptopropanol (DMP) : 0.99 g (0.008 mol)
2,2,6,6-Tetramethylenecyclohexyl pentapolyglycolate : 8.85 g (0.015 mol)

The molar proportion of DMP in the molar total of the monomers is 35%.

The product obtained has the following properties:
refractive index : 1.62
constringence (Abbe number) : 34
glass transition temperature : 135° C.

Example 5: Formation of a glass from the compound of formula (VIII) (prepared in Example 1)

The following are mixed at room temperature:
50 g of triallyl isocyanurate
50 g of sulfur compound of formula (VIII)
3 g of cyclohexyl peroxycarbonate.

The homogeneous mixture obtained is introduced into a space defined by a "Viton" ring seal (20 mm diameter, 2 mm thickness) placed between two plates of inorganic glass.

The polymerization reaction takes place in an oven programmed according to a heat cycle of approximately 16 h: the temperature is raised to 35° C. over 10 min, then to 55° C. over 1 h, then to 60° C. over 1 h; it is held at 60° C. for 10 h and the temperature is then raised to 65° C. over 20 min and then to 70° C. over 40 min, to 80° C. over 30 min, to 90° C. over 1 h and finally to 100° C. over 1 h. The temperature is then allowed to return to 20° C..

The glass obtained is transparent.
Its characteristics are as follows:
relative density=1.286
refractive index=1.568
Abbe number=44

(A glass based on diethylene glycol allyl carbonate has a relative density of 1.32, a refractive index of 1.50 and an Abbe number of 60).

Example 6: Formation of a glass from the compound of formula (VIII) (prepared in Example 1)

The following are mixed at room temperature:
25 g of triallyl isocyanurate
25 g of trimethylolpropane triacrylate
50 g of sulfur compound of formula (VIII)
3 g of cyclohexyl peroxycarbonate.

The homogeneous mixture obtained is introduced into a space defined by a "Viton" ring seal (20 mm diameter, 2 mm thickness) placed between two plates of inorganic glass.

The polymerization reaction takes place in an oven programmed according to a heat cycle of 16 h: the temperature is raised to 35° C. over 10 min, then to 55° C. over 1 h 50 min, then to 65° C. over 12 h, then the temperature is raised to 70° C. over 1 h and finally to 80° C. over 1 h. The temperature is then allowed to return to 20° C..

The glass obtained is transparent.
Its characteristics are as follows:
relative density=1.27
refractive index=1.565
Abbe number=40

Example 7: Formation of a glass from the compound formula (X) (prepared in Example 2B)

The following are mixed at room temperature:
50 g of triallyl isocyanurate
50 g of sulfur compound of formula (X)
3 g of cyclohexyl peroxycarbonate.

The homogeneous mixture obtained is introduced into a space defined by a "Viton" ring seal (20 mm diameter, 2 mm thickness) placed between two plates of inorganic glass.

The polymerization reaction takes place in an oven programmed according to a heat cycle of approximately 16 h: the temperature is raised to 35° C. over 10 min, then to 55° C. over 1 h, then to 60° C. over 1 h; it is held at 60° C. for 10 h, then the temperature is raised to 65° C. over 20 min, then to 70° C. over 40 min, to 80° C. over 0 min, to 90° C. over 1 h and finally to 100° C. over 1 h. The temperature is then allowed to return to 20° C.

The glass obtained is transparent.
Its characteristics are as follows:
relative density=1.271
refractive index=1.571
Abbe number=35.

Example 8: Formation of a glass from the compound of formula (X) (prepared in Example 2B)

The following are mixed at room temperature:
25 g of triallyl isocyanurate
25 g of trimethylolpropane triacrylate
50 g of sulfur compound of formula (X)
3 g of cyclohexyl peroxycarbonate.

The homogeneous mixture obtained is introduced into a space defined by a "Viton" ring seal (20 mm diameter, 2 mm thickness) placed between two plates of inorganic glass.

The polymerization reaction takes place in an oven programmed according to a heat cycle of 16 h: the temperature is raised to 35° C. over 10 min, then to 55° C. over 1 h 50 min, then to 65° C. over 12 h, then the temperature is raised to 70° C. over 1 h and finally to 80° C. over 1 h. The temperature is then allowed to return to 20° C.

The glass obtained is transparent.
Its characteristics are as follows:
relative density=1.27
refractive index=1.57
Abbe number=35

Example 9: Formation of a glass from the compound of formula (XII) (prepared in Example 3B)

The following are mixed at room temperature:
50 g of triallyl isocyanurate
50 g of sulfur compound of formula (XII)
3 g of tert-butyl 3,3,5-trimethylperhexanoate.

The homogeneous mixture obtained is introduced into a space defined by a "Viton" ring seal (20 mm diameter, 2 mm thickness) placed between two plates of inorganic glass.

The polymerization reaction takes place in an oven programmed according to a heat cycle of approximately 19 h: the temperature is raised to 40° C. over 8 min, then to 60° C. over 10 min, then to 85° C. over 1 h; the temperature is then raised from 85° to 95° C. during 16 h and finally to 105° C. over 1 h; 105° C. is then held for another 1 h. The temperature is then allowed to return to 20° C.

The glass obtained is transparent.
Its characteristics are as follows:
relative density=1.30
refractive index=1.582
Abbe number=30

Example 10: Formation of a glass from the compound of formula (XIII) (prepared in Example 4)

The following are mixed at room temperature:
50 g of triallyl isocyanurate
50 g of sulfur compound of formula (XIII)
3 g of tert-butyl 3,3,5-trimethylperhexanoate.

The homogeneous mixture obtained is introduced into a space defined by a "Viton" ring seal (20 mm diameter, 2 mm thickness) placed between two plates of inorganic glass.

The polymerization reaction takes place in an oven programmed according to a heat cycle of approximately 19 h: the temperature is raised to 40° C. over 8 min, then to 60° C. over 10 min, then to 85° C. over 1 h; the temperature is then raised from 85° to 95° C. during 16 h and finally to 105° C. over 1 h; 105° C. is held for a further 1 h. The temperature is then allowed to return to 20° C.

The glass obtained is transparent.

Its characteristics are as follows:
relative density=1.30
refractive index=1.55
Abbe number=40.

Example 11: Formation of a glass from the compound of formula (XII) (prepared in Example 3B)

The following are mixed at room temperature:
20 g of triallyl isocyanurate
40 g of divinylbenzene
40 g of sulfur compound of formula (XII)
3 g of tert-butyl 3,3,5-trimethylperhexanoate.

The homogeneous mixture obtained is introduced into a space defined by a "Viton" ring seal (20 mm diameter, 2 mm thickness) placed between two plates of inorganic glass.

The polymerization reaction takes place in an oven programmed according to a heat cycle of approximately 19 h: the temperature is raised to 40° C. over 8 min, then to 60° C. over 10 min, then to 85° C. over 1 h; the temperature is then raised from 85° to 95° C. during 16 h and finally to 105° C. over 1 h; 105° C. is held for a further 1 h. The temperature is then allowed to return to 20° C.

The glass obtained is transparent.
Its characteristics are as follows:
relative density=1.19
refractive index=1.589
Abbe number=30

Example 12: Formation of a glass from the compound of formula (XII) (prepared in Example 3B).

The following are mixed at room temperature:
20 g of triallyl isocyanurate
40 g of bisphenol A diacrylate
(bisphenol A=2,2-bis[hydroxyphenyl]propane)
40 g of sulfur compound of formula (XII)
3 g of tert-butyl 3,3,5-trimethylperhexanoate.

The homogeneous mixture obtained is introduced into a space defined by a "Viton" ring seal (20 mm diameter, 2 mm thickness) placed between two plates of inorganic glass.

The polymerization reaction takes place in an oven programmed according to a heat cycle of approximately 19 h: the temperature is raised to 40° C. over 8 min, then to 60° C. over 10 min, then to 85° C. over 1 h; the temperature is then raised from 85° to 95° C. during 16 h and finally to 105° C. over 1 h; 105° C. is held for a further 1 h. The temperature is then allowed to return to 20° C.

The glass obtained is transparent.
Its characteristics are as follows:
relative density=1.29
refractive index=1.583
Abbe number=30

Example 13: Formation of a glass from the compound of formula (XII) (prepared in Example 3B)

The following are mixed at room temperature:
1.22 g of xylylene diisocyanate
3.0 g of sulfur compound of formula (XII)
0.001 g of dibutyltin dilaurate.

The homogeneous mixture obtained is introduced into a space defined by a "Viton" ring seal (20 mm diameter, 2 mm thickness) placed between two plates of inorganic glass.

The polymerization reaction takes place in an oven programmed according to the following heat cycle:

3 hours' heating to change from room temperature to 80° C.,
3 hours' holding at 80° C.,
2 hours' heating to change from 80° C. to 130° C.,
3 hours' holding at 130° C.

The temperature is then allowed to drop back to 20° C.

The glass obtained is yellow and transparent.
Its characteristics are as follows:
refractive index=1.6118
Abbe number=29

We claim:

1. Sulfur compounds of general formula (I):

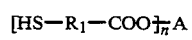

in which:
$R_1$ denotes a linear or branched alkylene radical containing 1 to 3 carbon atoms,
A denotes a hydrocarbon residue of valency n, chosen from the radicals of formulae:

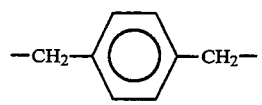

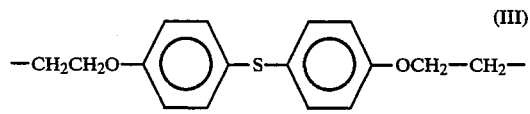

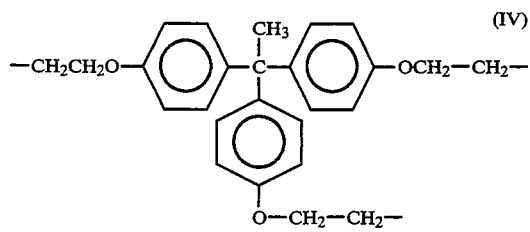

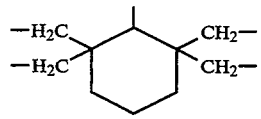

n denotes 2, 3 or 5.

2. Compounds of formula (I) according to claim 1, characterized in that $R_1$ denotes a methylene radical, an ethylene radical or an ethylidene radical.

3. Compounds of formula (I) according to either claim 1 or 2, characterized in that they are 1,4-benzenedimethylene di(thioglycolate), 4,4'-thiodiphenylene-1,1'-oxyethyl di(thioglycolate), 1,1,1-tris(4-phenylene-1-oxyethyl)ethane tri(thioglycolate), 2,2,6,6-tetramethylenecyclohexyl penta(thioglycolate), 1,4-benzenedimethylene di(2-mercaptopropionate), 4,4'-thiophenylene-1,1'-oxyethyl di(2-mercaptopropionate), 1,1,1-tris-(4-phenylene-1-oxyethyl)ethane tri(2-mercaptopropionate) or 2,2,6,6-tetramethylenecyclohexyl penta(2-mercaptopropionate).

4. Polythiourethanes characterized in that they are prepared by a reaction between at least one of the sulfur compounds of the formula (I) according to claim 3 and at least one polyisocyanate chosen from those in whose formula the —NCO groups are not bonded directly to an aromatic ring.

5. Polythiourethanes according to claim 4, characterized in that said at least one polyisocyanate is hexamethylene diisocyanate, 2-methyl-1,5-diisocyanatopentane, 2-ethyl-1,4diisocyanatobutane, isophorone diisocyanate, 4,4'-diisocyanatodicyclohexylmethane, hydrogenated xylylene diisocyanate, a trimer containing an isocyanurate ring or a biuret of such polyisocyanates.

6. Polythiourethanes according to claim 4, characterized in that the polyisocyanate is chosen from those which have a refractive index equal to or higher than 1.53.

7. Polythioethers characterized in that they are prepared by reaction between the sulfur compounds of formula (I) according to one of claim 1 and at least one compound containing at least two ethylenic unsaturations.

8. Polythioethers according to claim 7, characterized in that the compound containing ethylenic unsaturation is triallyl isocyanurate, triallyl cyanurate, diallyl phthalate, divinylbenzene, trimethallyl thiocyanurate, 2-hydroxyethyl cyanurate triacrylate, 2-hydroxyethyl cyanurate trimethacrylate, 2-hydroxyethyl cyanurate tri(allylcarbonate), 2-hydroxyethyl cyanurate tri(methallylcarbonate) or 2,2-bis(4-hydroxyphenyl)propane diacrylate.

9. Polythioethers according to claim 7, characterized in that a ternary mixture of polythiol/diunsaturated compound/acrylate or methacrylate compound selected from trimethylolpropane triacrylate, pentaerythritol triacrylate, pentaerythritol trimethacrylate, dipentaerythritol hexaacrylate or dipentaerythritol hexamethacrylate is used.

10. Polythioethers according to claim 8, characterized in that the reaction between the sulfur compounds of formula (I) and the compounds containing ethylenic unsaturations takes place with an excess of ethylenic unsaturations relative to the thiol functional groups.

11. Polythioethers according to claim 7, characterized in that their preparation takes place in the presence of a peroxide or radical generator catalyst.

12. Polythioethers according to claim 7, characterized in that during their preparation from 0.1% to 10% by weight of catalyst is employed relative to the weight of the reaction mixture.

13. Material useful for optical application comprising a polythiourethane of claim 4.

14. Polythiourethanes according to claim 5, characterized in that the polyisocyanate is chosen from those which have a refractive index equal to or higher than 1.53.

15. Polythioethers according to claim 8, characterized in that a ternary mixture of polythiol/diunsaturated compound/acrylate or methacrylate compound selected from trimethylolpropane triacrylate, pentaerythritol triacrylate, pentaerythritol trimethacrylate, dipentaerythritol hexaacrylate or dipentaerythritol hexamethacrylate is used.

16. Polythioethers according to claim 8 characterized in that the reaction between the sulfur compounds of formula (1) and the compounds containing ethylenic unsaturations takes place with an excess of ethylenic unsaturations relative to the thiol functional groups.

17. Polythioethers according to claim 9 characterized in that the reaction between the sulfur compounds of formula (1) and the compounds containing ethylenic unsaturations takes place with an excess of ethylenic unsaturations relative to the thiol functional groups.

18. Polythioethers according to claim 8, characterized in that their preparation takes place in the presence of a peroxide or radical generator catalyst.

19. Polythioethers according to claim 9, characterized in that their preparation takes place in the presence of a peroxide or radical generator catalyst.

20. Polythioethers according to claim 10, characterized in that their preparation takes place in the presence of a peroxide or radical generator catalyst.

21. Polythioethers according to claim 8, characterized in that, during their preparation, from 0.1% to 10% by weight of catalyst is employed relative to the weight of the reaction mixture.

22. Polythioethers according to claim 9, characterized in that, during their preparation, from 0.1% to 10% by weight of catalyst is employed relative to the weight of the reaction mixture.

23. Polythioethers according to claim 10, characterized in that, during their preparation, from 0.1% to 10% by weight of catalyst is employed relative to the weight of the reaction mixture.

24. Polythioethers according to claim 11, characterized in that, during their preparation, from 0.1% to 10% by weight of catalyst is employed relative to the weight of the reaction mixture.

25. Material useful for optical application comprising a polythiourethane of claim 5.

26. Material useful for optical application comprising a polythioether of claim 7.

27. Material useful for optical application comprising a polythioether of claim 8.

28. Material useful for optical application comprising a polythioether of claim 9.

29. A polythiourethane formed by the reaction of a sulfur compound of one of claim 1 and xylylene diisocyanate, toluene diisocyanate, 4,4'-diisocyanatodiphenylmethane, or polymeric 4,4'-diisocyanatodiphenylmethane.

30. A polythiourethane according to claim 9 formed by the reaction of a sulfur compound of one of claim 1 and xylylene diisocyanate.

31. A polythiourethane according to claim 4 further comprising at least one additional monomer bearing at least three functional groups that react with isocyanates to give carbamate functional groups, at least 40% of said functional groups being mercaptan groups and the mass of said mercaptan groups being at least 45% of the mass of the said additional monomer.

32. A polythiourethane according to claim 5 further comprising at least one additional monomer bearing at least three functional groups that react with isocyanates to give carbamate functional groups, at least 40% of said functional groups being mercaptan groups and the mass of said mercaptan groups being at least 45% of the mass of the said additional monomer.

33. A polythiourethane according to claim 29 further comprising at least one additional monomer bearing at least three functional groups that react with isocyanates to give carbamate functional groups, at least 40% of said functional groups being mercaptan groups and the mass of said mercaptan groups being at least 45% of the mass of the said additional monomer.

* * * * *

UNITED STATES PATENT AND TRADEMARK OFFICE
CERTIFICATE OF CORRECTION

PATENT NO. : 5,352,757  
DATED : October 04, 1994  
INVENTOR(S) : Sylvie LAVAULT et al.

Page 1 of 2

It is certified that error appears in the above-indentified patent and that said Letters Patent is hereby corrected as shown below:

On the title page:

Attorney, Agent, or Firm, front page, line 2 after "Farabow" insert --, Garrett--.

item [22] PCT No., front page "PCT/FR91/01014" Filed December 16, 1991

Claim 5, column 13, line 6 after "1,4" insert -- - --.

Claim 8, column 13, line 27 change "diacrylate" to --diacrylate--.

Claim 10, column 13, line 28 change "claim 8" to --claim 7--.

Claim 29, column 14, line 38 delete "of one".

Claim 30, column 14, line 42 change "claim 9" to --claim 29--.

Claim 30, column 14, line 43 delete "of one".

UNITED STATES PATENT AND TRADEMARK OFFICE
CERTIFICATE OF CORRECTION

PATENT NO. : 5,352,757
DATED : October 4, 1994
INVENTOR(S) : Sylvie Lavault, et al.

It is certified that error appears in the above-indentified patent and that said Letters Patent is hereby corrected as shown below:

Claim 30, column 14, line 43 delete "of one".

Signed and Sealed this

Ninth Day of May, 1995

Attest:

BRUCE LEHMAN

*Attesting Officer*     *Commissioner of Patents and Trademarks*